United States Patent [19]

Shepard

[11] Patent Number: 4,678,855

[45] Date of Patent: Jul. 7, 1987

[54] SUBSTITUTED BENZENESULFONAMIDES

[75] Inventor: Kenneth L. Shepard, North Wales, Pa.

[73] Assignee: Merck & Co., Inc., Rahway, N.J.

[21] Appl. No.: 785,924

[22] Filed: Oct. 9, 1985

[51] Int. Cl.[4] .................. C07C 149/443; A61K 9/06
[52] U.S. Cl. ........................................ 564/85; 560/9;
560/250; 548/576; 546/246; 558/33; 558/183;
558/184; 558/275; 544/327
[58] Field of Search .............. 564/85; 560/250, 9;
548/526; 546/246; 558/33, 183, 184, 275;
544/327

[56] References Cited

U.S. PATENT DOCUMENTS

| | | | |
|---|---|---|---|
| 3,927,093 | 12/1975 | Yale | 564/85 |
| 4,070,176 | 1/1978 | Oshio et al. | |
| 4,217,305 | 8/1980 | Imai et al. | |
| 4,510,325 | 4/1985 | Meyer et al. | 564/85 |

FOREIGN PATENT DOCUMENTS

| | | | |
|---|---|---|---|
| 1805778 | 11/1967 | Fed. Rep. of Germany | |
| 1338945 | 10/1963 | France | |
| 124758 | 7/1983 | Japan | 564/85 |
| 353734 | 6/1961 | Switzerland | 564/85 |
| 791923 | 3/1958 | United Kingdom | 564/85 |
| 791529 | 3/1958 | United Kingdom | 564/85 |

OTHER PUBLICATIONS

Kugita, *Chem. Pharm. Bull*, 10, 1001 (1962).

*Primary Examiner*—Anton H. Sutto
*Attorney, Agent, or Firm*—William H. Nicholson; Michael C. Sudol

[57] ABSTRACT

Benzenesulfonamides with a substituted-alkyl-$S(O)_n$-substituent are carbonic anhydrase inhibitors useful in the treatment of elevated intraocular pressure.

6 Claims, No Drawings

SUBSTITUTED BENZENESULFONAMIDES

SUMMARY OF THE INVENTION

This invention relates to novel benzenesulfonamides useful in the treatment of elevated intraocular pressure. More particularly this invention relates to compounds having the structural formula:

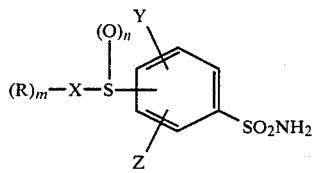

wherein R, X, Y, Z, m and n are hereinafter defined, as well as the pharmaceutically and ophthalmologically acceptable salts thereof. This invention also relates to pharmaceutical compositions and the use thereof for systemic and ophthalmic administration employing a novel compound of this invention as active ingredient for the treatment of elevated intraocular pressure, especially when accompanied by pathological damage such as in the disease known as glaucoma.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that render them unacceptable for chronic ocular use. (S)-1-tert-Butylamino-3-[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof.

To be an effective and acceptable topical agent, an ophthalmic carbonic anhydrase inhibitor must not only penetrate the ophthalmic tissues to reach the active sites within the eye, but it must also be devoid of those side effects including irritation, allergic reaction and the like which would militate against long term administration.

DETAILED DESCRIPTION OF THE INVENTION

The novel compounds of this invention have structural formula:

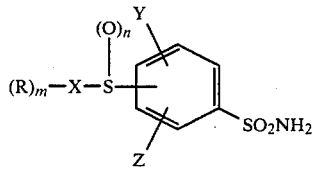

or a pharmaceutically acceptable salt thereof, wherein:

X is a straight, branched or cyclic, saturated or unsaturated hydrocarbon of up to 10 carbon atoms, such as

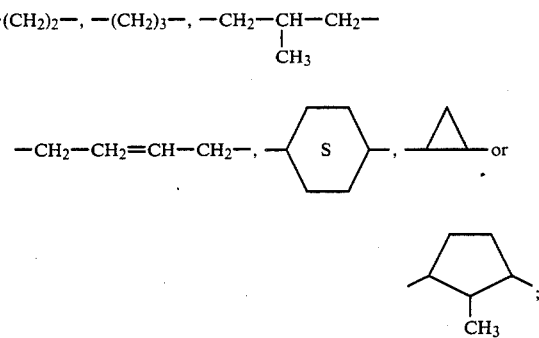

m is 1 or 2;
n is 0, 1 or 2;
R is
(1) —OR$^1$ wherein R$^1$ is
  (a) hydrogen,
  (b) C$_{1-4}$ alkyl,
  (c) hydroxy-C$_{1-4}$ alkyl,
  (d) C$_{1-4}$ alkoxy-C$_{1-4}$ alkyl,
  (e) carboxy-C$_{1-4}$ alkyl,
  (f) ω-amino-ω-carboxy-C$_{1-4}$ alkyl;

(2) 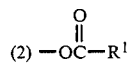

(3) 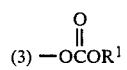

-continued (4) 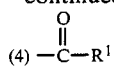

(5) 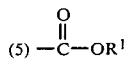

(6) 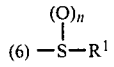

(7) —N(R$^1$)$_2$ wherein the R$^1$ groups are the same or different, and if loweralkyl, can be joined together to form, with the nitrogen atom to which they are attached, a 5- or 6-membered heterocycle such as piperidino, piperazino, morpholino, 1-pyrrolyl, or the like.

(8) 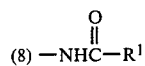

(9) 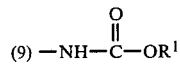

(10) phenyl, either unsubstituted or substituted with one or more of
 (a) hydroxy,
 (b) C$_{1-4}$ alkoxy,
 (c) C$_{1-5}$ alkanoyloxy,
 (d) halo, such as chloro or bromo,
 (e) C$_{1-4}$ alkyl,
 (f) —NR$^2$R$^3$, wherein R$^2$ and R$^3$ are independently,
  (i) hydrogen,
  (ii) alkyl, or
  (iii) C$_{1-5}$ alkanoyl,

(11) 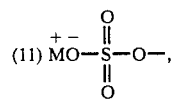

wherein
M$^+$ is an ophthalmologically acceptable cation selected from sodium, potassium ammonium, tetra(C$_{1-4}$alkyl)ammonium, pyridinium, imidazolium, pralidoxime, and thiamine

(12) 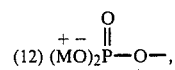

wherein M$^+$ is as previously defined;

(13) 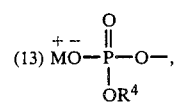

wherein R$^4$ is C$_{1-3}$ alkyl or phenyl —C$_{1-3}$ alkyl; or

(14) 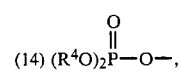

wherein R$^4$ is as previously defined, and the two may be the same or different.

Y and Z are independently;
(1) hydrogen,
(2) halo, such as chloro, bromo, or fluoro,
(3) nitro,
(4) —COOR$^5$ wherein R$^5$ is hydrogen, C$_{1-4}$ alkyl, or NR$^2$R$^3$,
(5) cyano,
(6) C$_{1-5}$alkanoyl,
(7) C$_{1-5}$alkyl,
(8) C$_{1-5}$alkylthio,
(9) C$_{1-5}$alkylsulfonyl,
(10) amino, or X can be joined with Y or Z to form a thieno group, a dihydrothieno group or the corresponding sulfones.

It is preferred that n=2, and that X be —(CH$_2$)$_{1-4}$—. It is also preferred that Y and Z be meta to the —SO$_2$NH$_2$ group and that

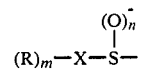

be para to the —SO$_2$NH$_2$ group.

The novel process of this invention comprises as the principal step the condensation reaction of a halo-sulfamoylbenzene with a mercaptan of formula (R)$_m$—X—SH under the influence of a strong base. The reaction may be illustrated as follows:

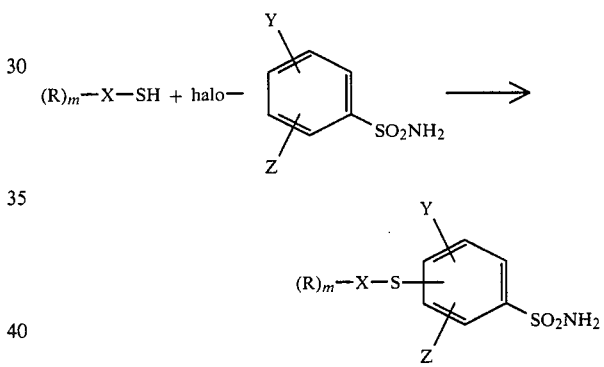

wherein halo is chloro, bromo or iodo, preferably bromo.

The benzene starting material is represented above as a benzenesulfonamide and is a quite useful reagent. However, the reaction is usually cleaner and better yields are achieved if the sulfonamide group is protected by an easily removed protecting group such as the N,N-dimethylformamidine. In other words, the starting material is preferably of structure:

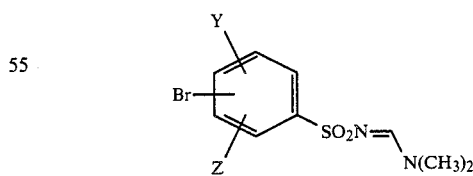

The formamidine protecting group is readily removed by treatment with a mineral acid or aqueous base.

In the novel process, the mercaptan, the halobenzene and strong base in approximately equimolar amounts are admixed in a polar organic solvent such as dimethylformamide, hexamethylphosphoramide, dimethylsulfoxide, or the like and stirred at about 10° C. to 100° C. for about 0.5 to 3 hours. The preferred laboratory technique is to treat the mercaptan with the strong base at about 10° C. to 30° C. followed by addition of the halobenzenesulfonamide with aging at about 10° C. to 100° C. for the requisite time period. Strong bases suitable for use in the novel process include alkali metal hydrides and alkoxides such as sodium, or potassium hydrides, methoxides, ethoxides, isopropoxides, or t-butoxides.

The sulfides produced by the foregoing process are converted to the corresponding sulfones by oxidation with hydrogen peroxide or a peracid such as m-chloroperbenzoic acid or Oxone R (a Dupont trade name for potassuim hydrogen monoperoxy-sulfate). Oxidation with hydrogen peroxide is conducted in a carboxylic acid medium such as acetic or propionic acid at about 50° to 100° C. for about 0.5 to 8 hours. The oxidation with a peracid is conducted in an inert organic solvent such as ethyl acetate, methanol, ethanol, butyl acetate, or isopropanol at about 10° to about 40° C. for about 1 to 24 hours. Clearly the time is not critical and times longer than that necessary to complete the reaction are not detrimental.

Oxidations with OXONE are conducted in water or aqueous alcohols at about 30° to 100° C. for about 1 to 5 hours.

A process to prepare those compounds wherein R is

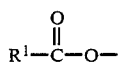

is represented by the following reaction scheme:

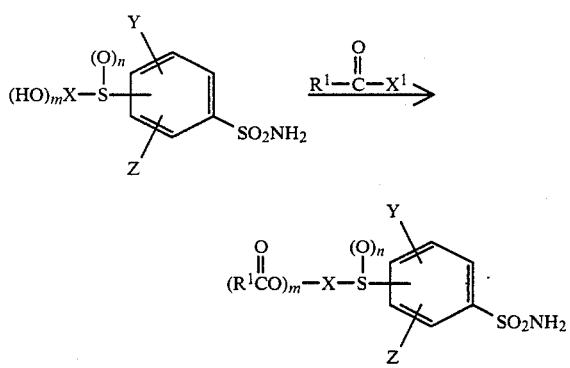

where $R^1$ has the meanings hereinbefore designated, and $X^1$ is chloro, bromo, iodo,

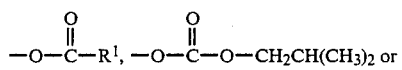

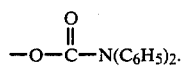

Generally equimolar amounts of the benzene and

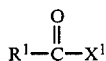

are employed, although use of an excess of the more readily available reactant is satisfactory.

The reaction is conducted in a suitable, inert solvent such as acetone, dimethylformamide, pyridine, ethyl acetate, tetrahydrofuran or benzene and the like with at least an equimolar amount of a hydrohalide acceptor when the acylating agent is an acyl halide or with a carboxylic acid acceptor when the acylating agent is an acid anhydride. Bases such as triethylamine, pyridine and the like may be employed for this purpose.

The reaction may be conducted with or without a catalyst at temperatures of from 0° C. to the boiling point of the solvent used but preferably from about 15° C. to 50° C.

When a catalyst is employed, a 4,4-dialkylaminopyridine such as 4-dimethylaminopyridine or 4-pyrrolidinopyridine is preferred.

The compounds wherein R is

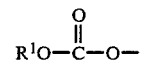

of this invention are most suitably prepared by reacting a compound

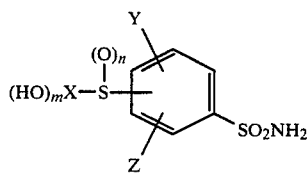

with an appropriate haloformate, particularly a chloroformate of the formula:

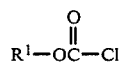

or a bis carbonate of the formula:

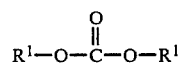

The reaction is conducted in a suitable solvent such as dimethylformamide, pyridine, acetone, ethyl acetate, tetrahydrofuran or benzene and the like with at least an equimolar amount of a hydrohalide acceptor. Bases such as triethylamine, pyridine and the like may be employed for this purpose.

The reaction may be conducted with or without a catalyst at temperatures of from 0° C. to the boiling point of the solvent used but preferably from 15° C. to 50° C.

When a catalyst is employed, triethylamine or a 4,4-dialkylaminopyridine such as 4-dimethylaminopyridine or 4-pyrrolidinopyridine is preferred.

Another process of this invention for preparing the ethers, i.e. $R=OR^1$ wherein $R^1=H$, the hydroxy compound is treated with an "alkylating" agent of formula $R^1-X^2$ wherein $X^2$ is a halide such as chloride, bromide or iodide, or other good leaving group such as mesylate, tosylate or benzenesulfonate in a suitable solvent such as dimethylformamide, hexamethylphosphoramide, or the like in the presence of a base such as an alkali metal alkoxide, preferably sodium methoxide, at about 0° C. to 35° C., usually about room temperature for about 10 to 30 hours.

The O-sulfates of this invention are prepared by reacting an hydroxyalkylsulfonylthiophene-2-sulfonamide with sulfamic acid in pyridine at elevated temperatures (about 50° C. to the boiling point) for about 18 to 48 hours to provide the ammonium salt followed, if desired, by titration with hydroxides of the formula MOH to provide the other salts.

Similarly the O-phosphates of this invention are prepared by treatment of a hydroxy compound with phosphorus oxychloride, an alkyl dichlorophosphate or a dialkyl chlorophosphate in pyridine or similar basic solvent at about $-5°$ to $+5°$ C. for about 0.25 to 1.0 hour.

In any of the foregoing syntheses the sulfonamide group may be protected as an N,N-disubstituted formamide prepared and removed as described earlier.

The novel pharmaceutical formulations of this invention include formulations for systemic administration and ophthalmic formulations designed for topical ocular administration, preferably the latter.

The formulations for systemic administration comprise a non-toxic pharmaceutically acceptable carrier and an effective amount of one or more of the novel compounds of this invention. They may be in a form (a) for oral administration; e.g., as tablets, in combination with other compounding ingredients customarily used such as talc, vegetable oils, polyols, benzyl alcohols, gums, gelatin, starches and other carriers; dissolved or dispersed or emulsified in a suitable liquid carrier; in hard or soft capsules, encapsulated in a suitable material; or (b) for parenteral administration; e.g., dissolved or dispersed in a suitable liquid carrier as a solution, suspension or emulsion, or (c) for transdermal application, e.g. as a patch.

The active drugs of this invention are most suitably administered in the form of ophthalmic pharmaceutical compositions adapted for topical administration to the eye such as a solution, suspension, ointment, gel or as a solid insert. Formulations of these compounds may contain from 0.01 to 15% and especially 0.5% to 2% of medicament. They may contain a novel compound of this invention as the sole medicament or may contain as well an effective amount of a β-adrenergic blocking agent such as timolol maleate or a parasympathomimetic agent such as pilocarpine. The two active principles are present in approximately equal amounts on a weight basis.

The pharmaceutical preparation which contains the active compound may be conveniently admixed with a non-toxic pharmaceutical inorganic or organic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert such as one which after dispensing the drug remains essentially intact, or a bio-erodible insert that either is soluble in lacrimal fluids, or otherwise disintegrates.

Generally, doses of the present compounds of about 0.01 to about 50 mg/kg and preferably from about 0.1 to about 20 mg/kg of body weight per day may be used. Dosage may be single or multiple depending on the daily total required and the unit dosage.

EXAMPLE 1

4-(2-Hydroxyethylthio)benzenesulfonamide

Step A

Preparation of N,N-Dimethyl-N'-(4-bromobenzenesulfonyl)formamidine

A solution of DMF dimethylacetal (16.5 g 0.14 mol) in acetonitrile (50 mL) was added dropwise to a stirred suspension of 4-bromobenzenesulfonamide (28.3 g, 0.12 mol) in acetonitrile (150 mL). After an additional hour, the solvent was removed and the residue was triturated with water, filtered and dried to give 34.4 g of white crystals, mp 141°–143° C.

Anal. Calc'd. for $C_9H_{11}BrN_2O_2S$ (291.182): C, 37.12; H, 3.81; N, 9.62. Found: C, 37.36; H, 3.80; N, 9.76.

Step B

Preparation of 4-(2-Hydroxyethylthio)benzene sulfonamide

A solution of 2-mercaptoethanol (58.6 g, 0.75 mol) in freshly degassed DMF (100 mL) was added dropwise under $N_2$ to a stirred mixture of NaH (34.5 g, 50% oil suspension, 0.75 mol) and DMF (400 mL). When gas evolution was complete, N,N-dimethyl-N'-(4-bromobenzenesulfonyl)formamidine (146 g, 0.50 mol) was added and the mixture was heated on the steam bath for one hour. The DMF was removed in vacuo and methanol (500 mL) and 10% (w/v) aqueous NaOH solution (500 mL) was added to the residue. This solution was warmed on the steam bath for one hour and the methanol removed. The residue was diluted with water (2500 mL) and washed with petroleum ether. The separated aqueous layer was acidified with concentrated HCl. The white solid that separated was filtered, washed with water and dried. Extraction of the aqueous filtrate with ethyl acetate produced an additional quantity of product; total yield, 112.4 g; mp 103°–108° C. Recrystallization of a sample from water followed by recrystallization from dichloroethane gave material with mp 111°–112° C.

Anal. Calc'd. for $C_8H_{11}NO_3S_2$ (233.308): C, 41.18; H, 4.75; N, 6.00. Found: C, 41.21; H, 4.83; N, 6.22.

Employing the procedure substantially as described in Example 1, but using as starting materials the mercaptans and 4-bromobenzenesulfonamides described in Table I, there are produced the substituted thiobenzene sulfonamides also described in Table I in accordance with the following reaction scheme.

TABLE I

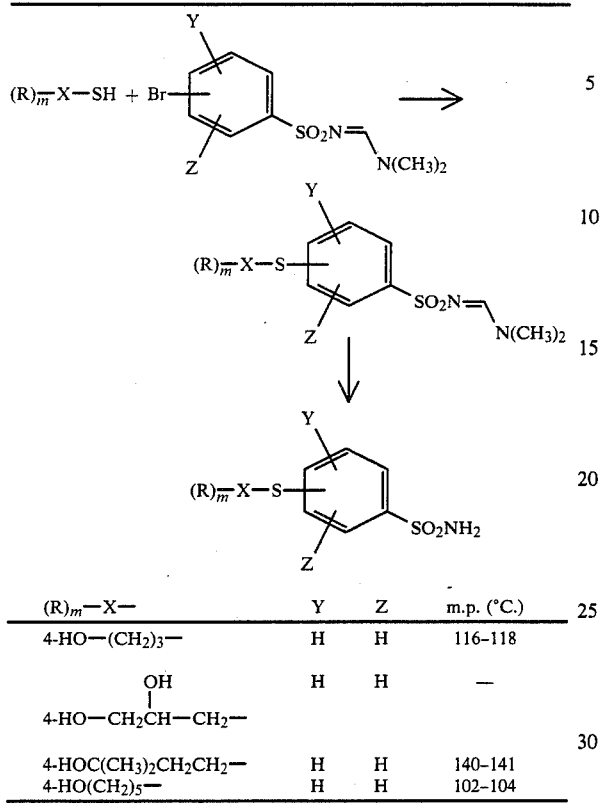

| (R)$_m$—X— | Y | Z | m.p. (°C.) |
|---|---|---|---|
| 4-HO—(CH$_2$)$_3$— | H | H | 116–118 |
| 4-HO—CH$_2$CH(OH)—CH$_2$— | H | H | — |
| 4-HOC(CH$_3$)$_2$CH$_2$CH$_2$— | H | H | 140–141 |
| 4-HO(CH$_2$)$_5$— | H | H | 102–104 |

EXAMPLE 2

4-(2-Hydroxyethylsulfonyl)benzenesulfonamide 4-(2-Hydroxyethylthio)benzenesulfonamide (94.3 g, 0.40 mol) was added portionwise to a stirred solution of Oxone ® (368.9 g, 0.60 mols) in H$_2$O (3600 mL). After 18 hours the white solid was collected, washed with H$_2$O and dried to give 72.6 g, mp 156°–162° C. An additional 12.3 g was obtained from the aqueous filtrate by extraction with ethyl acetate (3×1000 mL). Recrystallization from acetonitrile gave material with mp 163°–165° C.

Anal. Calc'd. for C$_8$H$_{11}$NO$_5$S$_2$ (265.31): C, 36.21; H, 4.18; N, 5.28. Found: C, 36.26; H, 4.14; N, 5.34.

EXAMPLE 3

4-(2,3-Dihydroxypropylsulfonyl)benzenesulfonamide

A solution of m-chloroperbenzoic acid (19.35 g, 80–85% pure, 0.09 mol) in ethyl acetate (100 mL) was added dropwise with stirring to a solution of 4-(2,3-dihydroxypropylthio)benzenesulfonamide (11.5 g, 0.044 mol) in methanol (100 mL). After 3 hours the mixture was evaporated to dryness, the residue was triturated with ether and the resulting solid was collected and dried, 4.32 g, mp 140°–147° C., and recrystallized from 2-propanol.

Anal. Calc'd. for C$_9$H$_{13}$NO$_6$S$_2$ (295.33): C, 36.60; H, 4.44; N, 4.74. Found: C, 36.80; H, 4.42; N, 4.72.

Employing the procedure substantially as described in Example 2 or 3 but using as starting materials the substituted thiobenzenesulfonamides described in Table II, there are produced the substituted sulfonylbenzenesulfonamides also described in Table II in accordance with the following reaction scheme.

TABLE II

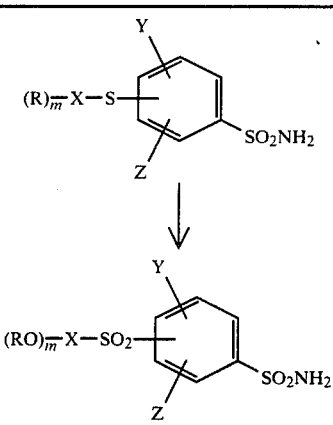

| (R)$_m$—X— | Procedure of Example | Y | Z | m.p. (°C.) |
|---|---|---|---|---|
| HO—(CH$_2$)$_3$— | 2 | H | H | 149–151 |
| HOC(CH$_3$)$_2$(CH$_2$)$_2$— | 2 | H | H | 140–141 |
| HO(CH$_2$)$_5$— | 2 | H | H | 102–104 |

EXAMPLE 4

4-(2-Hydroxyethylthio)-3-nitrobenzenesulfonamide

A mixture of 2-mercaptoethanol (1.66 g, 0.02 mol), anhydrous sodium acetate (2 g) and 4-chloro-3-nitrobenzenesulfonamide (2.37 g, 0.01 mol) was heated on the steam bath for about 5 hours. The reaction mixture was diluted with water, acidified with 6N hydrochloric acid and cooled. Filtration and drying gave 2.11 g of a yellow solid that was recrystallized from ethyl acetate, m.p. 150°–152° C.

Anal. Calc'd for C$_8$H$_{10}$N$_2$O$_5$S$_2$: C, 34.52; H, 3.62; N, 10.07. Found: C, 34.68; H, 3.56; N, 10.03.

Employing the procedure substantially as described in Example 4, but employing as starting material the mercapto compounds described in Table III, there are produced the nitrophenylthioethers also described in Table III in accordance with the following reaction scheme.

TABLE III

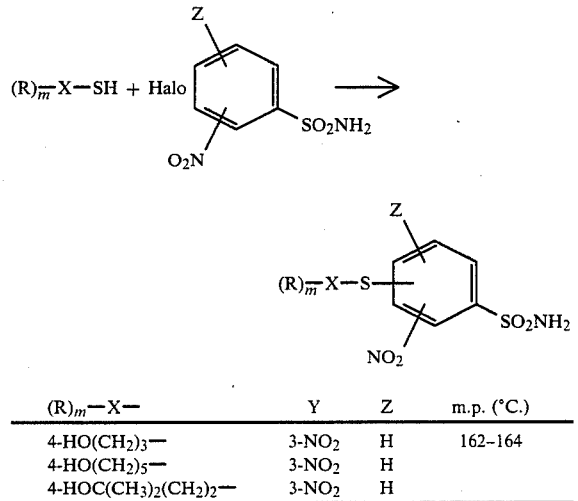

| (R)$_m$—X— | Y | Z | m.p. (°C.) |
|---|---|---|---|
| 4-HO(CH$_2$)$_3$— | 3-NO$_2$ | H | 162–164 |
| 4-HO(CH$_2$)$_5$— | 3-NO$_2$ | H | |
| 4-HOC(CH$_3$)$_2$(CH$_2$)$_2$— | 3-NO$_2$ | H | |

EXAMPLE 5

4-(3-Hydroxypropylsulfonyl)-3-nitrobenzenesulfonamide

A mixture of Oxone ® (28 g, 0.0463 mol) and 4-(3-hydroxypropylthio)-3-nitrobenzenesulfonamide (6.77 g, 0.0232 mol) in 300 ml H₂O was heated on a steambath for about 2 hours. Crystallization occured as the clear solution cooled. Filtration and drying gave 5.91 g of a white solid m.p. = 168°–170°.

Anal. Calc'd. for $C_9H_{12}N_2O_7S_2$: C, 33.33; H, 3.73; N, 8.64. Found: C, 33.45; H, 3.69; N, 8.76.

Employing the procedure substantially as described in Example 5, but substituting as starting material the alkylthio-nitrobenzene sulfonamides described in Table IV there are produced the sulfones also described in Table IV in accordance with the following reaction scheme:

TABLE IV

| $(R)_m$—X— | Y | Z | m.p. (°C.) |
|---|---|---|---|
| 4-HO(CH₂)₂— | 3-NO₂ | H | |
| 4-HO(CH₂)₅— | 3-NO₂ | H | |
| 4-HOC(CH₃)₂(CH₂)₂— | 3-NO₂ | H | |

EXAMPLE 6

4-(3-hydroxypropylsulfonyl)-3-aminobenzenesulfonamide

A mixture of 4-(3-hydroxypropylsulfonyl)-3-nitrobenzenesulfonamide (4.0 g, 0.012 mol), iron powder (11 g), and 12M HCl (0.6 ml) in 10 ml water and 40 ml ethanol was refluxed on a steam bath for about 2 hours. The reaction mixture was filtered hot, and the solvent evaporated. The residue was taken up in ethyl acetate, washed with water, saturated sodium bicarbonate, water, then brine. After drying, evaporation of solvent left a residue that quickly crystallized. The solid was washed with water and collected. Recrystallization from butanol left 2.0 g of a white solid. M.p. = 136.5°–138° C.

Anal. Calc'd for $C_9H_{14}N_2O_5S_2$: C, 36.42; H, 4.79; N, 9.52. Found: C, 36.57; H, 4.79; N, 9.54.

Employing the procedure substantially as described in Example 6, but using as starting materials, the nitro compounds described in Table V there are produced the amino compounds also described in Table V in accordance with the following reaction:

TABLE V

| $(R)_m$—X— | Starting Y | Product Y | Z | m.p. (°C.) |
|---|---|---|---|---|
| 4-HO(CH₂)₂— | 3-NO₂ | 3-NH₂ | H | 128–130 |
| 4-HO(CH₂)₅ | 3-NO₂ | 3-NH₂ | H | |
| 4-HOC(CH₃)₂(CH₂)₂ | 3-NO₂ | 3-NH₂ | H | |

EXAMPLE 7

4-(3-hydroxypropylthio)-3-carboxybenzenesulfonamide

Step A

Preparation of N,N-Dimethyl-N'-(4-chloro-3-methoxycarbonylbenzenesulfonyl)formamidine To a suspension of 4-chloro-3-methoxy-carbonylbenzenesulfonamide (1.0 g, 0.004 mol) in acetonitrile (10 ml), DMF dimethylacetal (0.477 g, 0.004 mol) was added dropwise. The mixture was stirred about 1 hour then solvent was evaporated to give a tan solid. Recrystallization from butylchloride gave 0.65 g white solid. M.p. = 139.5°–141° C.

Anal. Calc'd for $C_{11}H_{13}ClN_2O_4S$: C, 43.35; H, 4.30; N, 9.19. Found: C, 43.79; H, 4.31; N, 9.56.

Step B

Preparation of 4-(3-hydroxypropylthio)-3-carboxybenzenesulfonamide

Sodium hydride (2.35 g, 50% oil suspension, 0.049 mol) was washed twice with petroleum ether than suspended in freshly degassed DMF (130 ml). 3-Mercaptopropanol (4.51 g, 0.049 mol) was added dropwise under nitrogen. When gas evolution ceased, N,N-dimethyl-N'-(4-chloro-3-methoxycarbonyl)benzene-sulfonyl)formamidine (9.96 g, 0.0327 mol) was added and the mixture was heated in an oil bath at 80° C. for about 3 hours. The DMF was removed in vacuo and the residue treated with 10% sodium hydroxide (100 ml). After about 15 minutes the reaction mixture was acidified with 3N HCl. The white solid that separated was recrystallized from water to give 1.48 g. m.p. 204°–205.5° C.

Anal. Calc'd for $C_{10}H_{13}NO_5S_2$: C, 41.22; H, 4.50; H, 4.81. Found: C, 41.31; H, 4.59; N, 4.93.

Employing the procedure substantially as described in Example 7, but using as starting materials in Step B thereof, the mercaptoalkanols described in Table VI, there are produced the thio ethers also described in Table VI in accordance with the following reaction scheme:

TABLE VI

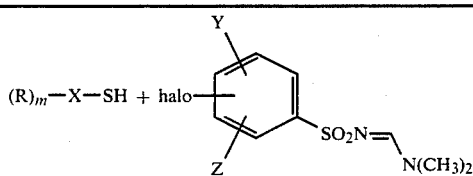

| (R)$_m$—X— | Starting Y | Product Y | Z | m.p. (°C.) |
|---|---|---|---|---|
| 4-HOC(CH$_3$)$_2$(CH$_2$)$_2$— | 3-CH$_3$OOC— | 3-HOOC— | H | 186–187 |
| 4-HO(CH$_2$)$_2$— | 3-CH$_3$OOC— | 3-HOOC— | H | 128–130 |

EXAMPLE 8

4-(3-hydroxypropylthio)-3-methoxycarbonylbenzenesulfonamide 4-(3-hydroxypropylthio)-3-carboxybenzene-sulfonamide (15 g, 0.0515 mol) and concentrated H$_2$SO$_4$ (4 ml) were dissolved in methanol (150 ml) and refluxed on a steam bath for about 5 hours. The solvent was removed and the residue was treated with water. The mixture was extracted with ethylacetate, which was washed with water, saturated sodium bicarbonate, water and brine. After drying, removal of the solvent left a tannish solid. Recrystallization from 1,2-dichloroethane gave 13.5 g of a white solid. M.p.=123°–125°.

Anal. Calc'd. for C$_{11}$H$_{15}$NO$_5$S$_2$: C, 43.26; H, 4.95; N, 4.59. Found: C, 43.45; H, 4.95; N, 4.69.

Similarly prepared were:
4-(3-hydroxy-3,3-dimethylpropylthio)-3-methoxycarbonylbenzenesulfonamide;
4-(2-hydroxyethylthio)-3-methoxycarbonylbenzenesulfonamide.

EXAMPLE 9

4-(3-hydroxypropylsulfonyl)-3-methoxycarbonylbenzenesulfonamide

A mixture of 4-(3-hydroxypropylthio)-3-methoxycarbonylbenzenesulfonamide (8.3 g, 0.027 mol) and Oxone® (24 g, 0.04 mol) in water (200 ml) was stirred at room temperature for 24 hours. The solution was extracted 3 times with ethyl acetate and the combined extracts were washed with water and brine. Drying and removal of the solvent left an oily residue which, when treated with boiling 1,2-dichloroethane gave a white solid. After collection and drying, 5.0 g of a solid was obtained. M.p.=124.5°–126° C.

Anal. Calc'd for C$_{11}$H$_{15}$NO$_7$S$_2$: C, 39.16; H, 4.48; N, 4.15. Found: C, 38.82; H, 4.40; N, 4.23.

Similarly prepared was:
4-(2-hydroxyethylsulfonyl)-3-methoxycarbonylbenzenesulfonamide

EXAMPLE 10

4-(3-hydroxypropylsulfonyl)-3-carboxybenzenesulfonamide

A mixture of 4-(3-hydroxypropylthio)-3-carboxybenzenesulfonamide (2.89 g, 0.01 mol) and Oxone® (9.15 g, 0.015 mol) in water (50 ml) was heated to 65° C. for about 1 hour. The solution was cooled and extracted with ethyl acetate. The organic extracts were combined and washed with brine. After drying and removal of solvent 2.40 g of an oil remained. The oil was treated with saturated NaCl solution and a white solid was collected. Recrystallization from a small amount of ethyl acetate gave 0.84 g of white solid. M.p.=170°.

Anal. Calc'd for C$_{10}$H$_{13}$NO$_7$S$_2$: C, 37.14; H, 4.05; N, 4.33. Found: C, 37.58; H, 4.17; N, 4.26.

Similarly prepared was:
4-(3-hydroxy-3,3-dimethylpropylsulfonyl)-3-carboxybenzenesulfonamide, m.p. 175°–176° C.

EXAMPLE 11

4-(2-Hydroxyethylthio)-3-fluorobenzenesulfonamide

Step A

Preparation of 3,4-difluorobenzenesulfonamide

Chlorosulfonic acid (50 ml, 0.752 mol) was placed in a vessel and 1,2-difluorobenzene (20 g, 0.1753 mol) was added quickly from a pipette such that vigorous gas evolution occurred. The solution was heated (80° C.) for about 20 minutes then quenched over 300 g of ice. After 20 minutes of stirring the mixture was allowed to settle and the supernatant decanted. The white, waxy solid was treated with about 300 ml of concentrated NH$_4$OH, stirred ½ hour, filtered to remove insoluble material and the resulting filtrate was acidified with concentrated HCl. Extraction wtih ethyl acetate, drying over anhydrous MgSO$_4$, and solvent removal gave a white solid (26 g) that when recrystallized from butyl chloride gave white plates. M.p.=89°–91° C.

Step B

Preparation of N,N-Dimethyl-N'-(3,4-difluorobenzenesulfonyl)formamidine

To a suspension of 3,4-difluorobenzenesulfonamide (20.94 g, 0.108 mol) in acetonitrile (200 ml), DMF dimethylacetal (14.8 g, 0.125 mol) was added dropwise. The mixture was stirred about 1 hour, after which the solvent was evaporated to leave 23.5 g of white solid. Recrystallization from butyl chloride gave a solid with m.p. 109°–112° C.

Step C

Preparation of 4-(2-hydroxyethylthio)-3-fluorobenzenesulfonamide

Sodium hydride (1.11 g, 50% oil dispersion, 0.023 mol) was washed with petroleum ether then suspended in freshly degassed DMF (50 ml). 2-Mercaptoethanol (1.8 g, 0.023 mol) was added dropwise under nitrogen. When gas evolution ceased, N,N-Dimethyl-N'-(3,4-difluorobenzenesulfonyl)formamidine (5 g, 0.02 mol) was added and the mixture was heated in an oil bath about 2 hours (80° C.). DMF was removed in vacuo and the residue was treated with 100 ml of 10% NaOH. After an additional hour of stirring the solution was acidified with concentrated HCl and extracted with ethylacetate (2×100 ml), and dried over anhydrous magnesium sulfate. Removal of solvent left 3 g of a white solid which when recrystallized from butyl chloride had m.p.=109°–111° C.

Employing the procedure substantially as described in Example 11, but using as starting materials the mercaptans and 4-bromobenzene-sulfonamides described in Table VII there were prepared the substituted thiobenzenesulfonamides also described in Table VII in accordance with the following reaction scheme:

TABLE VII

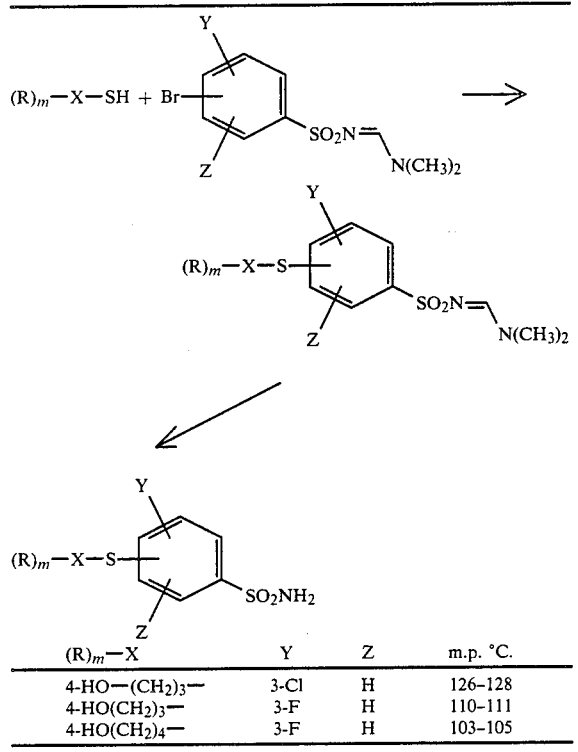

| (R)$_m$—X | Y | Z | m.p. °C. |
|---|---|---|---|
| 4-HO—(CH$_2$)$_3$— | 3-Cl | H | 126–128 |
| 4-HO(CH$_2$)$_3$— | 3-F | H | 110–111 |
| 4-HO(CH$_2$)$_4$— | 3-F | H | 103–105 |

EXAMPLE 12

4-(2-Hydroxyethylsulfonyl)-3-fluorobenzenesulfonamide

A mixture of Oxone ® (17.6 g, 0.029 mol) and 4-(2-hydroxyethylthio)-3-fluorobenzenesulfonamide (6.0 g, 0.024 mol) in 150 ml H$_2$O was stirred at room temperature for about 5 hours. The mixture was extracted with ethyl acetate (2×100 ml) and the organic portion washed with brine. After drying with anhydrous magnesium sulfate the solvent was removed to give 5 g white solid. Recrystallization from water gave a solid with m.p.=164°–166° C.

Following the procedure substantially as described in Example 12, but using as starting materials the hydroxyalkylthiobenzene sulfonamides described in Table VII there are produced the hydroxyalkylsulfonylbenzene sulfonamides described in Table VIII in accordance with the following reaction scheme:

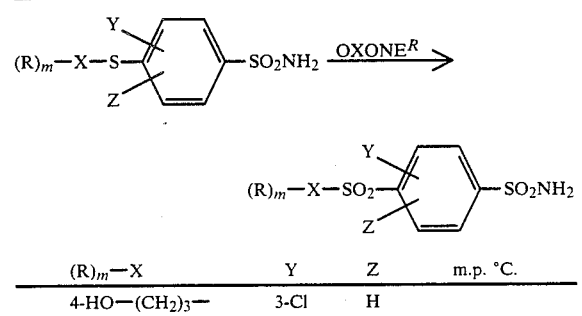

| (R)$_m$—X | Y | Z | m.p. °C. |
|---|---|---|---|
| 4-HO—(CH$_2$)$_3$— | 3-Cl | H | |
| 4-HO(CH$_2$)$_3$— | 3-F | H | 129–131 |
| 4-HO(CH$_2$)$_4$— | 3-F | H | 126–127 |

EXAMPLE 13

| 4-(3-hydroxypropylsulfonyl) benzenesulfonamide (I) | 1 mg. | 15 mg. |
|---|---|---|
| Monobasic sodium phosphate.2H$_2$O | 9.38 mg. | 6.10 mg. |
| Dibasic sodium phosphate.12H$_2$O | 28.48 mg. | 16.80 mg. |
| Benzalkonium chloride | 0.10 mg. | 0.10 mg. |
| Water for injection q.s. ad. | 1.0 ml. | 1.0 ml. |

Compound I, phosphate buffer salts, and benzalkonium chloride are added to and dissolved in water. The pH of the composition is adjusted to 6.8 and diluted to volume. The composition is rendered sterile by ionizing radiation.

EXAMPLE 14

| 4-(2-hydroxyethylsulfonyl) benzenesulfonamide (II) | 5 mg. |
|---|---|
| petrolatum q.s. ad. | 1 gram |

Compound II and the petrolatum are aseptically combined.

EXAMPLE 15

| 4-(3-hydroxypropylsulfonyl) benzenesulfonamide | 1 mg. |
|---|---|
| Hydroxypropyl cellulose q.s. | 12 mg. |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

EXAMPLE 16

| 4-(3-hydroxypropylsulfonyl) benzenesulfonamide | 1 mg. |
|---|---|
| Hydroxypropyl cellulose q.s. ad. | 12 mg. |

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R. H. cabinet until it is pliable. Appropriately sized inserts are cut from the film.

EXAMPLE 17

| 4-(3-hydroxypropylsulfonyl)benzene- | 1 mg. |

| | |
|---|---|
| sulfonamide | |
| Hydroxypropylmethyl cellulose q.s. ad. | 12 mg. |

Ophthalmic inserts are manufactured from a solvent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R. H. cabinet until it is pliable. Appropriately sized inserts are then cut from the film.

EXAMPLE 18

| | |
|---|---|
| 4-(3-hydroxypropylsulfonyl)benzene-sulfonamide | 1 mg. |
| Hydroxypropylmethyl cellulose q.s. ad. | 12 mg. |

Ophthalmic inserts are manufactured from compression molded films which are prepared on a Carver Press by subjecting the powdered mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R. H. at 30° C.) for two to four days. After removal from the humidity cabinet, the vials are stoppered and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and to insure against recontamination, the sterilization is preferably conducted after packaging. The best mode of sterilizing is to employ ionizing radiation including radiation emanating from Cobalt 60 or high energy electron beams.

What is claimed is:

1. A compound of structural formula:

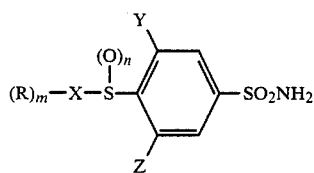

or an ophthalmologically acceptable salt thereof, wherein:

X is a straight, branched or cyclic, saturated hydrocarbon of up to 10 carbon atoms,
m is 1 or 2;
n is 0, 1 or 2;
R is
(1) —OH,

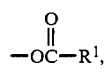

wherein $R^1$ is hydrogen or $C_{1-4}$alkyl,

(4) —N($R^1$)$_2$ wherein the $R_1$ groups are the same or different, and if loweralkyl, can be joined together to form, with the nitrogen atom to which they are attached, a 5- or 6-membered heterocycle,

wherein M+ is an ophthalmologically acceptable cation selected from sodium, potassium ammonium, tetra($C_{1-4}$alkyl)ammonium, pyridinium, imidazolium, pralidoxime, and thiamine

wherein M+ is as previously defined;

wherein $R^4$ is $C_{1-3}$ alkyl or phenyl —$C_{1-3}$ alkyl; or

wherein $R^4$ is as previously defined, and the two may be the same or different.

Y and Z are independently;
(1) hydrogen,
(2) halo, such as chloro, bromo, or fluoro,
(3) nitro,
(4) $C_{1-5}$alkanoyl,
(5) $C_{1-5}$alkyl,
(6) $C_{1-5}$alkylthio,
(7) $C_{1-5}$alkylsulfonyl, or
(8) amino.

2. The compound of claim 1 or an ophthalmologically acceptable salt thereof, wherein n is 2, X is —(CH$_2$)—$_{1-4}$, and R is

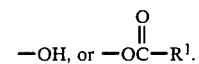

3. The compound of claim 2 or an ophthalmologically acceptable salt thereof, wherein Y and Z are independently hydrogen or halo.

4. An ophthalmic formulation for the treatment of elevated intraocular pressure comprising an ophthalmologically acceptable carrier and an effective intraocular pressure lowering amount of the compound of claim 1 or an ophthalmologically acceptable salt thereof.
5. The formulation of claim 4, wherein n is 2, X is —(CH$_2$)—$_{1-4}$, and R is
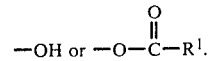
6. The formulation of claim 5, wherein Y and Z are independently hydrogen or halo.
* * * * *